(12) United States Patent
D'Angelo et al.

(10) Patent No.: US 10,576,223 B2
(45) Date of Patent: Mar. 3, 2020

(54) UNLOCKING A RESPIRATORY THERAPY MODE

(75) Inventors: Mark D'Angelo, Harrison City, PA (US); John Raymond Pujol, Murrysville, PA (US)

(73) Assignee: KONINKLIJKE PHLIPS N.V., Eindhoven (NL)

( * ) Notice: Subject to any disclaimer, the term of this patent is extended or adjusted under 35 U.S.C. 154(b) by 1144 days.

(21) Appl. No.: 14/125,663

(22) PCT Filed: Jun. 13, 2012

(86) PCT No.: PCT/IB2012/052976
§ 371 (c)(1),
(2), (4) Date: Dec. 12, 2013

(87) PCT Pub. No.: WO2012/172491
PCT Pub. Date: Dec. 20, 2012

(65) Prior Publication Data
US 2014/0102455 A1   Apr. 17, 2014

Related U.S. Application Data

(60) Provisional application No. 61/497,239, filed on Jun. 15, 2011.

(51) Int. Cl.
*A61M 16/00* (2006.01)
*G16H 40/40* (2018.01)
(Continued)

(52) U.S. Cl.
CPC .... *A61M 16/0051* (2013.01); *A61M 16/0057* (2013.01); *A61M 16/024* (2017.08); *A61M 16/06* (2013.01); *A61M 16/0875* (2013.01); *G16H 40/40* (2018.01); *A61M 2016/0027* (2013.01); *A61M 2016/0033* (2013.01);
(Continued)

(58) Field of Classification Search
CPC .. A61M 16/00; A61M 16/0051; A61M 16/10; A61M 2205/27; A61M 2205/276; A61M 2205/3553; A61M 2205/50; A61M 2205/005
See application file for complete search history.

(56) References Cited

U.S. PATENT DOCUMENTS

2002/0036601 A1\* 3/2002 Puckeridge ....... A61M 16/0051
345/55
2002/0077856 A1   6/2002 Pawlikowski
(Continued)

FOREIGN PATENT DOCUMENTS

CN       1736324 A    2/2006
WO    WO0132069 A2    5/2001
(Continued)

*Primary Examiner* — Valerie L Woodward

(57) ABSTRACT

A respiratory therapy device is configured, e.g. by a care provider, such that a second therapy mode different from the current therapy mode is unlocked, under predetermined circumstances and a third therapy mode different from the current and the second therapy mode is unlocked, under predetermined circumstances. The user of a given respiratory therapy device may activate the unlocked second or third therapy mode. The second or the third therapy mode may expire after a predetermined amount of usage, and be deactivated.

19 Claims, 5 Drawing Sheets

(51) Int. Cl.
*A61M 16/06* (2006.01)
*A61M 16/08* (2006.01)

(52) U.S. Cl.
CPC .............. *A61M 2205/3365* (2013.01); *A61M 2205/3553* (2013.01); *A61M 2205/3584* (2013.01); *A61M 2205/50* (2013.01); *A61M 2205/502* (2013.01); *A61M 2205/52* (2013.01); *A61M 2205/60* (2013.01)

(56) References Cited

U.S. PATENT DOCUMENTS

| | | | |
|---|---|---|---|
| 2005/0217674 A1 | 10/2005 | Burton | |
| 2007/0000491 A1* | 1/2007 | Chalvignac | A61M 16/0051 128/204.23 |
| 2007/0113849 A1 | 5/2007 | Matthews | |
| 2007/0193583 A1* | 8/2007 | Reed | A61M 16/00 128/204.18 |
| 2009/0107498 A1 | 4/2009 | Plattner | |
| 2010/0108064 A1 | 5/2010 | Blackwell | |
| 2010/0218766 A1* | 9/2010 | Milne | A61M 16/0051 128/204.23 |
| 2012/0291783 A1* | 11/2012 | Peiris | A61M 16/0051 128/204.21 |
| 2012/0304995 A1* | 12/2012 | Kauc | A61M 16/00 128/204.23 |

FOREIGN PATENT DOCUMENTS

| | | |
|---|---|---|
| WO | WO2010099375 A1 | 9/2010 |
| WO | WO2011004274 A1 | 1/2011 |
| WO | WO2011021118 A1 | 2/2011 |

\* cited by examiner

UNLOCKING A RESPIRATORY THERAPY MODE

CROSS-REFERENCE TO RELATED APPLICATIONS

This patent application claims the priority benefit under 35 U.S.C. § 371 of international patent application no. PCT/IB2012/052976, filed Jun. 13, 2012, which claims the priority benefit under 35 U.S.C. § 119(e) of U.S. Provisional Application No. 61/497,239 filed on Jun. 15, 2011, the contents of which are herein incorporated by reference.

BACKGROUND OF THE INVENTION

1. Field of the Invention

The present disclosure pertains to methods and systems to configure respiratory therapy modes in respiratory therapy devices.

2. Description of the Related Art

Treating respiratory disorders, including sleep apnea, with pressure support therapy is known. In particular, the use of constant positive airway pressure (CPAP) therapy is common. Some subjects may have experience respiratory disturbances, despite adhering to e.g. a CPAP therapy mode. In other words, a (prescribed) therapy mode may not be effective for all subjects.

SUMMARY OF THE INVENTION

One or more embodiments of the present disclosure relate to providing a system to configure respiratory therapy modes for users of respiratory therapy devices. The system includes a data gathering module, a provider interface module, and a device configuration module. The data gathering module is configured to receive usage information related to a given respiratory therapy device in a first therapy mode. The provider interface module is configured to receive a first unlock selection while the given respiratory therapy device in set on the first therapy mode, the first unlock selection indicating that a second therapy mode should be unlocked. The device configuration module is configured such that, responsive to reception of first the unlock selection, the device configuration module activates the second therapy mode. The device configuration module is further configured such that, responsive to reception of a second unlock selection, the device configuration module activates the third therapy mode and, wherein the device configuration module is further configured to deactivate the third therapy mode after a predetermined trial period has expired.

It is yet another aspect of one or more embodiments to provide a method for configuring respiratory therapy modes for users of respiratory therapy devices. The method includes receiving usage information related to a given respiratory therapy device, representing therapeutic usage of the given device in a first therapy mode; receiving a first unlock selection indicating that a second therapy mode should be unlocked; responsive to reception of the first unlock selection, activating the second therapy mode for the given device; receiving a second unlock selection indicating that a third therapy mode should be unlocked; responsive to reception of the second unlock selection, activating the third therapy mode for the given device; and deactivating the third therapy mode after a predetermined trial period has expired.

It is yet another aspect of one or more embodiments to provide a system for configuring respiratory therapy modes for users of respiratory therapy devices. The system includes means for receiving usage information related to a given respiratory therapy device; means for receiving a first unlock selection indicating that a second therapy mode should be unlocked; means for activating the second therapy mode for the given device, responsive to reception of the unlock selection; means for receiving a second unlock selection indicating that a third therapy mode should be unlocked; means for activating the third therapy mode for the given device, responsive to reception of the second unlock selection; and means for deactivating the third therapy mode after a predetermined trial period has expired.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
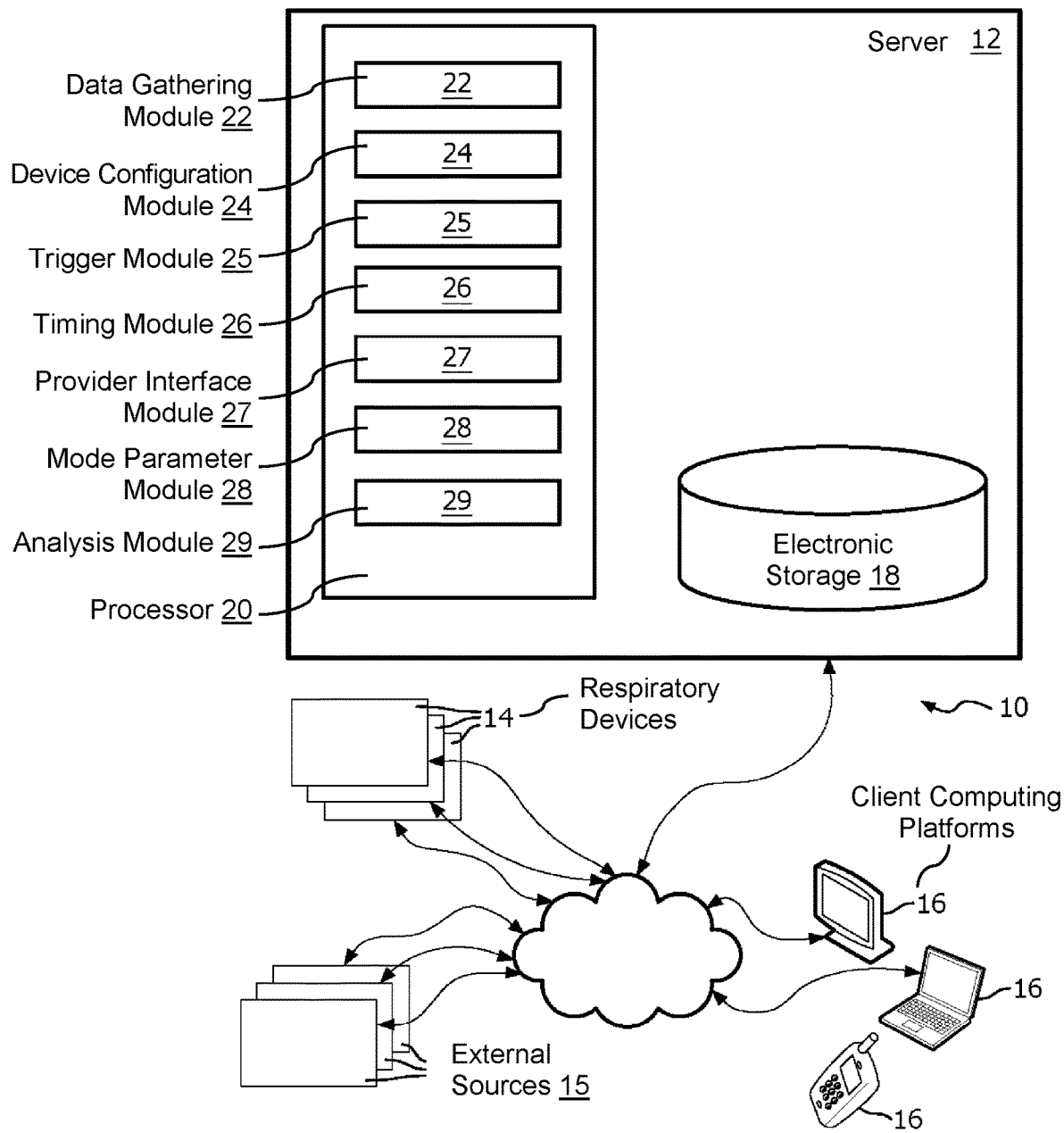
FIG. 1 schematically illustrates a system to configure respiratory therapy modes for users of respiratory therapy devices.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 to configure respiratory therapy modes for users of respiratory therapy devices 14. A respiratory therapy device 14 may connect to a server 12 to facilitate the exchange of information, including configuration commands. Adherence to a therapy regimen involving a respiratory therapy device 14 may be challenging for some subjects. Given a predetermined set of circumstances, commonly including, e.g., a measure representing insufficient effectiveness of, or adherence to, a first therapy mode, a care provider may decide that a subject should use, at least for a trial period, a second therapy mode that is different from the first therapy mode. The first therapy mode may be referred to as the original mode, the default mode, and/or the initial mode.

A "mode" of a respiratory therapy device broadly defines the range of capabilities, pertaining to inhalation pressure levels and exhalation pressure levels, that the respiratory therapy device can perform. Examples of therapy modes may include one or more of a CPAP mode, a multi-pressure (e.g., bi-level) mode using a BiPAP device available from Philips Respironics, an auto-titration mode in which the pressure (CPAP) or pressures (IPAP and/or EPAP) various based on the monitored condition of the patient, and/or other modes. Some therapy modes are capable of auto-titration, whereas other modes are not. The commands may further dictate one or more mode parameters for a therapy mode of the device. Mode parameters may affect the operation of respiratory therapy device 14 in a particular therapy mode in a persistent manner, i.e. for more than one respiratory cycle. Examples of mode parameters are a constant pressure level, an inspiratory pressure level, an expiratory pressure level, and/or other parameters that affect the operation of respiratory therapy device 14 whilst in a particular therapy mode.

System 10 may include one or more servers 12, respiratory devices 14, and/or other components. System 10 may operate in communication and/or coordination with one or more external sources 15. Users, including care providers, may interface with system 10 and/or respiratory therapy devices 14 via client computing platforms 16. The components of system 10, servers 12, respiratory therapy devices 14, and/or client computing platforms 16 may be operatively linked via one or more electronic communication links. For example, such electronic communication links may be established, at least in part, via one or more networks such as the Internet and/or other networks. It will be appreciated that this is not intended to be limiting, and that the scope of this disclosure includes implementations in which servers 12, respiratory therapy devices 14, and/or client computing platforms 16 may be operatively linked via some other communication media. The components of system 10 may be integrated into fewer or more devices than shown in FIG. 1. The described functionality of the components of system 10 may be distributed across partitions different from the one shown in FIG. 1. For example, the user interface for a care provider may be integrated into a respiratory therapy device.

As is discussed further below with respect to FIG. 2, respiratory therapy devices 14 are capable of configuration in accordance with one or more embodiments. The respiratory therapy devices may be configured locally (using a UI, smart card, and/or other local technique, device, or process, for configuration, or combination thereof), or remotely (using one or more networks, and/or other remote technique, device, or process, for configuration or combination thereof), and/or both. Configuration may be under control of (automated) programming, or may be under control of a care provider, and/or a combination of both.

A given respiratory therapy device 14 is configured to provide respiratory therapy through the supply of a pressurized flow of breathable gas to subject 106 in accordance with a therapeutic respiratory regimen. Respiratory therapy may be delivered in different therapy modes. A therapy device manufacturer, distributor, and/or operator may have different compensation requirements, or costs, for subjects. For example, the cost of CPAP therapy may be less than certain types of multi-level pressure support therapy. The cost assigned to a therapy mode may be a function of sophistication, comfort, effectiveness, efficiency, and/or other parameters. Configuration of respiratory therapy devices 14 that are capable of providing different modes of respiratory therapy may provide an efficient procedure for testing respiratory therapies (in terms of effectiveness, comfort, and/or other usage parameters) for individual subjects.

A given client computing platform 16 may include one or more processors configured to execute computer program modules. The computer program modules may be configured to enable one or more users (e.g. care providers) associated with the given client computing platform 16 to interface with system 10 and/or respiratory therapy devices 14, and/or provide other functionality attributed herein to client computing platforms 16. By way of non-limiting example, the given client computing platform 16 may include one or more of a desktop computer, a laptop computer, a handheld computer, a NetBook, a Smartphone, a gaming console, and/or other computing platforms. Alternatively, and/or simultaneously, a given client computing platform 16 may be integrated in or embedded in a user's respiratory therapy device 14.

External resources 15 may include sources of information, external entities participating with system 10, therapeutic devices, and/or other resources. In some implementations, some or all of the functionality attributed herein to external resources 15 may be provided by resources included in system 10.

Server 12 may configure, or cooperate with client computing platforms 16 to configure, one or more respiratory therapy modes for users of respiratory therapy devices 14. Server 12 may include electronic storage 18, one or more processors 20, and/or other components. Server 12 may include communication lines, or ports to enable the exchange of information with one or more networks and/or other computing platforms.

Electronic storage 18 may comprise electronic storage media that electronically stores information. The electronic storage media of electronic storage 18 may include one or both of system storage that is provided integrally (i.e., substantially non-removable) with server 12 and/or removable storage that is removably connectable to server 12 via, for example, a port (e.g., a USB port, a FireWire port, etc.) or a drive (e.g., a disk drive, etc.). Electronic storage 18 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 18 may store software algorithms, information determined by processor 20, information obtained, identified, gathered, and/or provided by one or more computer program modules, information received from server 12, information received from client computing platforms 16, information received from respiratory therapy devices 14, and/or other information that enables server 12 to function properly.

Processor(s) 20 is configured to provide information processing capabilities in server 12. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination.

As is shown in FIG. 1, processor 20 may be configured to execute one or more computer program modules. The one or more computer program modules may include one or more of a data gathering module 22, a device configuration module 24, a trigger module 25, a timing module 26, a provider interface module 27, a mode parameter module 28, an analysis module 29, and/or other modules. Processor 20 may be configured to execute modules 22, 24, 25, 26, 27, 28, and/or 29 by software; hardware; firmware; some combination of software, hardware, and/or firmware; and/or other mechanisms for configuring processing capabilities on processor 20.

It should be appreciated that although modules 22, 24, 25, 26, 27, 28, and 29 are illustrated in FIG. 1 as being co-located within a single processing unit, in implementations in which processor 20 includes multiple processing units, one or more of modules 22, 24, 25, 26, 27, 28, and/or 29 may be located remotely from the other modules. The description of the functionality provided by the different modules 22, 24, 25, 26, 27, 28, and/or 29 described below is for illustrative purposes, and is not intended to be limiting, as any of modules 22, 24, 25, 26, 27, 28, and/or 29 may provide more or less functionality than is described. For example, one or more of modules 22, 24, 25, 26, 27, 28, and/or 29 may be eliminated, and some or all of its functionality may be provided by other ones of modules 22, 24, 25, 26, 27, 28, and/or 29. As another example, processor 20 may be configured to execute one or more additional modules that may perform some or all of the functionality attributed below to one of modules 22, 24, 25, 26, 27, 28, and/or 29.

It will be appreciated that the illustration of modules 22, 24, 25, 26, 27, 28, and/or 29 being executed solely on processor 20 separate from client computing platforms 16 and respiratory therapy devices 14 is not intended to be limiting. For example, in some implementations, the client computing platforms 16 may be configured to provide locally at least some of the functionality attributed above to one or more of modules 22, 24, 25, 26, 27, 28, and/or 29. Similarly, one or more of modules 22, 24, 25, 26, 27, 28, and/or 29 may be executed locally on individual client computing platforms 16 while others are executed on server 12. As another example, in some implementations, the respiratory therapy devices 14 may be configured to provide locally at least some of the functionality attributed above to one or more of modules 22, 24, 25, 26, 27, 28, and/or 29. Similarly, one or more of modules 22, 24, 25, 26, 27, 28, and/or 29 may be executed locally on individual respiratory therapy devices 14 while others, if present, may be executed remotely from individual respiratory therapy devices 14.

Data gathering module 22 is configured to receive usage information related to one or more respiratory therapy devices 14. Receiving usage information may include receiving transmission from one or both of a given respiratory therapy device 14 and/or a given client computing platform 16. The received usage information represents therapeutic usage of the given device in its current therapy mode, i.e. the therapy mode that is currently active. For example, a given respiratory therapy device 14 may operate in a CPAP therapy mode and transmit daily, weekly, or monthly usage information. The usage information may include the total hours of cumulative therapeutic usage during the previous 24 hours. Usage information may be associated with either a particular respiratory therapy device 14, a particular subject, or both.

Usage information may include one or more of a therapy starting date, user experience level, an average duration of daily usage, a usage pattern, metrics indicating quality of therapy and/or quality of sleep, level of compliance with a therapy regimen, therapeutic device characteristics (e.g. mask type or settings of respiratory therapy device 14), derived usage characteristics, user-stated usage characteristics, and/or other usage information. User-stated usage characteristics may include issues or problems the user is experiencing while undergoing therapy, and/or other user-stated usage characteristics. Derived usage characteristics may include low and/or irregular usage (as detected e.g. through analysis of usage reports), decreasing average daily usage, excessive mask leak, and/or other derived usage characteristics. Respiratory therapy device 14 may (autonomously and/or periodically) compile a usage report and submit it to server 12.

Timing module 26 may be configured to determine whether a threshold amount of therapeutic usage time (and/or calendar time) has elapsed for one or more respiratory therapy devices 14. For a given device, a threshold amount of time may include one or both of a cumulative usage threshold and/or a consecutive usage threshold. For example, system 10 may be configured to switch from one therapy mode to another therapy mode only after at least a predetermined number of hours of therapeutic usage have occurred, and/or at least a predetermined number of hours of consecutive therapeutic usage have occurred. Alternatively, and/or simultaneously, timing module 26 may be configured to determine whether a trial period (e.g. for a trial therapy mode) has expired. A trial period may be specified in calendar days, usage days, and/or other time-based metrics, and/or any combination thereof. Operation of constituent components of system 10, e.g. device configuration module 24 and/or data gathering module 22, may be responsive to a determination by timing module 26.

Timing module 26 may be configured to cooperate with a timing module internal to a given respiratory therapy device 14. For example, once a trial mode of therapy is activated in a given respiratory therapy device 14, the determination that the trial period has expired may be made independently by a given respiratory therapy device 14, without requiring the respiratory therapy device 14 to interact with system 10 or a network (e.g. the EncoreAnywhere network).

Analysis module 29 may be configured to determine a respiratory disturbance index (RDI), a sleep quality index, and/or other indexes or information related to the effectiveness and/or efficiency of the therapy provided by respiratory therapy device 14. The index(es) and/or information may be determined by analysis module 29 based on received usage information.

Analysis module 29 may be configured to determine the RDI by adding together the number of apneas, the number of hypopneas, and the number of respiratory effort related arousals (RERAs) in a given time period. RDI may be interpreted as a measure for the efficiency of a particular respiratory therapy. A determination made by analysis module 29 may be used in other constituent components of system 10, e.g. trigger module 25.

Trigger module 25 may be configured to determine whether a trigger event occurred pertaining to a given respiratory therapy device 14, its user, and/or both. For example, a trigger event may include detection that a subject is experiencing many respiratory disturbances in spite of undergoing respiratory therapy, receiving notification from respiratory therapy device 14 that a subject is experiencing many respiratory disturbances in spite of undergoing respiratory therapy, determinations based on received usage information, instructions and/or commands received from a care provider, and/or other events. An occurrence of a trigger event may include one or more conditions that need to be satisfied simultaneously and/or consecutively. For example, a trigger event may include a usage threshold (e.g. determined by timing module 26).

A trigger event may be based on operation of analysis module 29, which may determine (autonomously, without explicit intervention from a care provider and/or a user) that the current therapy mode is not sufficiently effective and/or efficient. In some implementations, trigger module 25 is configured to detect a trigger event responsive to RDI (and/or some other index or parameter) determined by analysis module 29 crossing a threshold. The threshold may be a predetermined threshold, may be set based on a per-user basis, may be set manually by a caregiver, and/or determined in other ways. In some implementations, trigger module 25 is configured to detect a trigger event responsive to a minimum amount of usage time per day for a predetermined number of consecutive days. This predetermined number may be any number between 2 and 20. The occurrence of a trigger event may be used by other constituent components of system 10 to perform a particular predetermined action.

Trigger module 25 may take into account whether a subject has undergone a particular mode of respiratory therapy using more than one mask. In some embodiments, a therapy mode should not be unlocked unless a predetermined number of different masks have been used by the subject, e.g. for a threshold amount of time. Logical combinations of basic trigger events to form more complex trigger events are contemplated.

Trigger module 25 may be configured to allow a care provider to manually override the determination whether a trigger event occurred. Alternatively, and/or simultaneously, a care provider may be able to override (remotely) any operational settings, including therapy mode and parameters, for any of the respiratory therapy devices 14.

Mode parameter module 28 may be configured to determine parameters of a therapy mode, including, but not limited to, one or more pressure levels, a respiratory rate, a tidal volume, and/or other parameters. Mode parameter module 28 may provide one or more recommended parameters of a particular respiratory therapy, such as one or more pressure levels, to be included in the commands from device configuration module 24 to a given respiratory therapy device 14. Mode parameter module 28 may be configured to automatically update target parameters and/or recommended parameters for a therapy mode based on information gathered during therapeutic usage of respiratory therapy device 14.

Device configuration module 24 is configured to interact with respiratory therapy devices 14 to adjust operation of respiratory therapy devices 14. This includes adjusting one or more of a therapy mode, one or more parameters of a therapy mode, and/or other aspects/features of the operation of respiratory therapy devices 14. In some embodiments, responsive to reception of an unlock selection through provider interface module 27, device configuration module 24 activates a subsequent therapy mode. In an exemplary embodiment, device configuration module 27 deactivates the second therapy mode after a predetermined trial period has expired or when a subsequent unlock selection is received.

For the purpose of this disclosure, "unlocking" a therapy mode may mean "making available for use and/or selection," "download instructions that implement said therapy mode," and/or other ways to enable a therapy mode on a respiratory therapy device that prior to the enablement was not available for use and/or selection. Activation and/or deactivation may require user interaction, or it may happen automatically without requiring user interaction. The unlocked second therapy mode may be a premium therapy mode, such as bi-level, auto-titration, and/or other premium therapy modes.

Mode parameter module 28 may determine one or more mode parameters for the activated second or third therapy mode based on usage information received by data gathering module 22 during the original therapy mode. Device configuration module 24 may further dictate one or more determined mode parameters of the second or third therapy mode for the given device. The (transmitted) command may further dictate the period and/or condition after which the unlocked second or third therapy mode should be deactivated. For example, an unlocked and activated multi-pressure level therapy mode may expire after a trial period of 60 calendar days.

Device configuration module 24 may (re)activate the original therapy mode after expiration of a trial period of the second or the third therapy mode. Mode parameter module 28 may determine one or more updated mode parameters for the (re)activated original therapy mode based on usage information received by data gathering module 22 during any (combination) of preceding therapy modes. The (transmitted) command to (re)activate the original therapy mode may further dictate one or more determined updated mode parameters for the (re)activated original therapy mode for the given device.

As noted above, device configuration module 24 may activate a third therapy mode after expiration of a trial/usage period of the second therapy mode, such that the third therapy mode is different from the second therapy mode, as well as the original therapy mode. Mode parameter module 28 may determine one or more updated mode parameters for the newly activated third therapy mode based on usage information received by data gathering module 22 during any (combination) of preceding therapy modes. The (transmitted) command to activate the third therapy mode may further dictate one or more determined updated mode parameters for the third therapy mode for the given device. For example, the original, second, and third therapy modes may include CPAP therapy, bi-level therapy, and auto-titrating (e.g. AutoCPAP), respectively.

Device configuration module 24 may be configured to respond to the determination that a trigger event occurred. For example, a trigger event may be the determination that the current mode of respiratory therapy is not sufficiently effective to treat a particular type of respiratory disorder for a given subject. In response to this determination, device configuration module 24 may, e.g. in conjunction with provider interface module 27 and/or mode parameter module 28, unlock and/or activate a second or third mode of respiratory therapy for the respiratory therapy device 14 associated with the given subject.

Provider interface module 27 is configured to receive a first unlock selection from a given care provider while the respiratory therapy device 14 is set on the first therapy mode. The first unlock selection may indicate that a second therapy mode should be unlocked. Through the generated user interface, a given care provider is able to unlock one or more therapy modes for individual respiratory therapy devices 14. The generated user interface is configured to present information to a caregiver and/or receive selection/entries from the caregiver that enable the caregiver to manage (remotely and/or locally) the therapy a subject receives from an individual respiratory therapy device 14. Such information and/or selections may include a subject identification, a respiratory therapy device identification, a therapy mode identifier, a therapy selection, trigger information, usage information, and/or other information, as well as other selections. In some embodiments, a selectable acceptance field may be activated, e.g., responsive to reception of the first unlock selection, wherein user selection of the selectable acceptance field indicates acceptance of the second therapy mode.

Responsive to such user selection of the selectable acceptance field, provider interface module 27 (or another constituent component of system 10) may cause device configuration module 24 to activate the second or third therapy mode. The described functionality may thus "unlock" a therapy mode responsive to the trigger event and selection by the caregiver. The (transmitted) command may result in automatic initiation of operating respiratory therapy device 14 in the second therapy mode. The (transmitted) command may result in other actions or operations by respiratory therapy device 14 that facilitate provision of pressure therapy in the second therapy mode to the subject.

Provider interface module 27 may be configured to respond to the determination that a trigger event occurred. For example, presenting a first or second or subsequent unlock selection to a care provider (and/or receiving a first or second or subsequent unlock selection from a care provider) may be responsive to the determination that a trigger event occurred.

Figure 3:
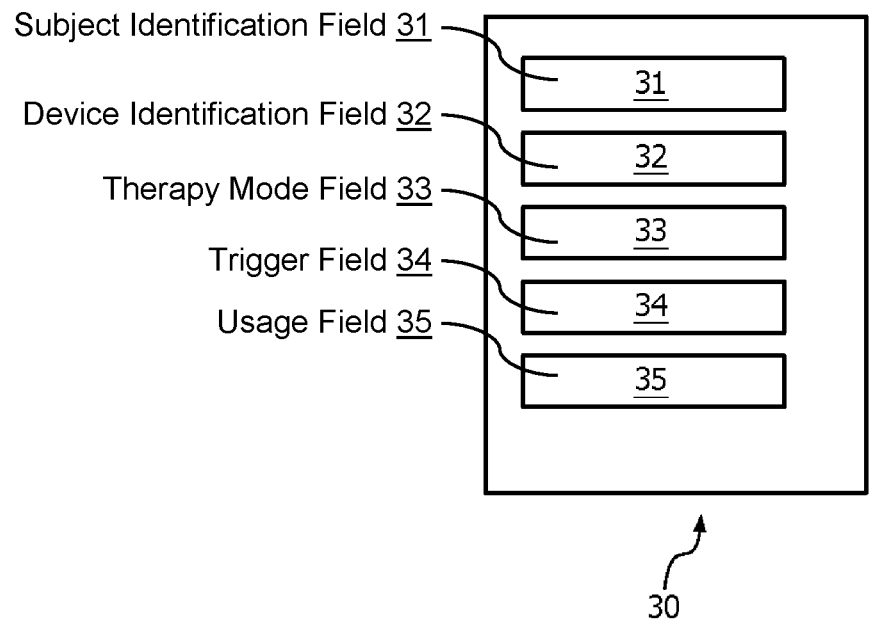
FIG. 3 illustrates an exemplary embodiment of a user interface, according to one or more embodiments.

By way of illustration, FIG. 3 illustrates an exemplary embodiment of a user interface 30 presented by provider interface module 27, e.g. through a client computing platform 16, according to one or more embodiments. A care provider may use a given client computing platform 16 to interact with system 10 and provider interface module 27. User interface 30 may include one or more fields configured to receive entry and/or selection of information pertaining to operational parameters and/or conditions of a given respiratory therapy device 14. Field 31 may be a subject identification field configured to present an identifier of the current subject associated with a given respiratory therapy device 14. Field 32 may be a device identification field configured to present an identifier of the given respiratory therapy device 14. Field 33 may be a therapy mode/unlock field configured to present the current therapy mode (and/or any of the parameters/settings associated with the current therapy mode) for a given respiratory therapy device 14. Field 33 may, optionally responsive to the occurrence of a trigger event, present a first or second or subsequent unlock selection, e.g., labeled with an identifier and/or representation of a second/third or other therapy mode that is different from the current therapy mode.

Selecting the first unlock selection may activate the second therapy mode for a given respiratory therapy device 14 (either indefinitely or for a trial period). Unlocking a second therapy mode may mean presenting the user of the given respiratory therapy device 14 with a selectable acceptance field (e.g. in a user interface of the given respiratory therapy device) to activate, upon selection, the unlocked second therapy mode. Field 34 may be a trigger field configured to present information pertaining to the occurrence of trigger events. For example, field 34 may present information pertaining to the determined, measured, estimated, and/or approximated effectiveness of the current therapy mode. Field 35 may be a usage field configured to present usage information to a user. For example, field 35 may present the average number of hours of nightly usage of a given respiratory therapy device 14.

Referring back to FIG. 1, in some embodiments, trigger module 25 is configured to determine whether a time-out trigger event occurred, pertaining to a given respiratory therapy device 14, its user, and/or both. Occurrence of a time-out trigger event may be based on one or more of a cumulative usage threshold, a consecutive usage threshold, a number of usage days, a number of calendar days, a target date, and/or other predetermined periods and/or thresholds. Responsive to the occurrence of a time-out trigger event (e.g. expiration of a predetermined trial period), device configuration module 24 may deactivate the previously unlocked (second/third) therapy mode. As a result, the respiratory therapy device 14 can no longer operate using the second/third therapy mode. Instead, operation of the respiratory therapy device 14 reverts to the therapy mode that was active prior to activating the unlocked second therapy mode, a.k.a. the original therapy mode or may revert to another, as yet not used, therapy mode.

Figure 2:
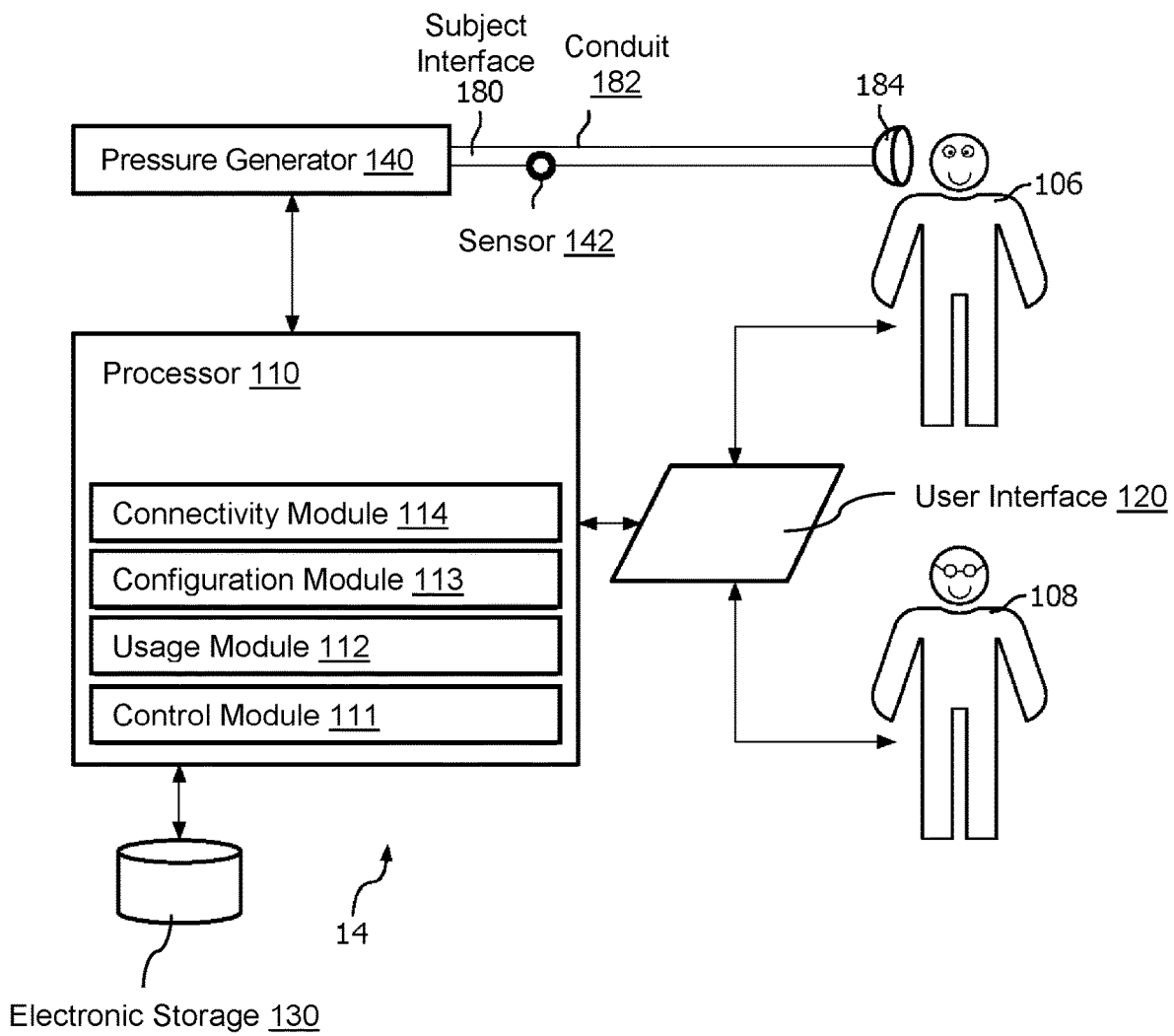
FIG. 2 schematically illustrates a respiratory therapy device capable of configuration in accordance with one or more embodiments.

FIG. 2 schematically illustrates a respiratory therapy device 14 that is capable of configuration in accordance with one or more embodiments. Respiratory therapy device 14 may comprise one or more of a pressure generator 140, a processor 110, a sensor 142, an electronic storage 130, a user interface 120, a subject interface 180, and/or other constituent components.

Pressure generator 140 is configured to provide a pressurized flow of breathable gas to the airway of subject 106, e.g. via subject interface 180. Subject 106 may or may not initiate one or more phases of respiration. Pressure support may be implemented as a higher and lower positive pressure of a (multi-level) respiratory therapy device 14. For example, to support inspiration, the pressure of the pressurized flow of breathable gas is adjusted to an Inspiratory Positive Air Pressure (IPAP). Similarly, to support expiration, the pressure of the pressurized flow of breathable gas is adjusted to an Expiratory Positive Air Pressure (EPAP). Other schemes for providing respiratory support (including bi-level pressure support) through the delivery of the pressurized flow of breathable gas are contemplated. Note that a pressure level need not be constant throughout an entire phase of respiration.

Respiratory therapy device 14 may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. Respiratory therapy device 14 may be configured to provide types of therapy including types of therapy where a subject performs inspiration and/or expiration of his own accord or where the device provides negative airway pressure.

A therapy "session" of using a respiratory therapy device 14 may be defined as a period of consecutive therapeutic usage of the respiratory therapy device 14, not to exceed 24 consecutive hours. If the respiratory therapy is used to treat sleeping disorders, such as sleep apnea, the related session length may correspond to the sleeping pattern of a subject. A typical session length may thus be at least 6-8 hours. In some modes of respiratory therapy, one or more pressure levels are adjusted on a relatively ongoing manner (e.g., each breath, every few breaths, every few seconds, etc.) during an individual therapy session to titrate the therapy. In other modes of therapy, adjustments may be made only between sessions rather than during sessions.

A pressurized flow of breathable gas is delivered from pressure generator 140 to or near the airway of subject 106 by a subject interface 180. Subject interface 180 includes a conduit 182, a subject interface appliance 184, and/or other components. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 is configured to deliver the pressurized flow of breathable gas to the airway of subject 106. As such, subject interface appliance 184 may include any appliance suitable for this function. In certain embodiments, pressure generator 140 is a dedicated ventilation device and subject interface appliance 184 is configured to be removably coupled with another interface appliance being used to deliver respiratory therapy to subject 106. For example, subject interface appliance 184 is configured to engage with and/or be inserted into an endotracheal tube, a tracheotomy portal, and/or other interface appliances. In certain embodiments, subject interface appliance 184 is configured to engage the airway of subject 106 without an intervening appliance. In this embodiment, subject interface appliance 184 includes one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Respiratory therapy device 14 may include electronic storage 130 comprising electronic storage media that electronically stores information. The electronic storage media of electronic storage 130 includes one or both of system storage that is provided integrally (i.e., substantially non-removable) with respiratory therapy device 14 and/or removable storage that is removably connectable to respiratory therapy device 14 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media.

Electronic storage 130 stores software algorithms, information determined by processor 110, information received via user interface 120, and/or other information that enables respiratory therapy device 14 to function properly. For example, electronic storage 130 may record or store timing information (including duration of inhalation phases and exhalation phases as well as transitional moments), one or more (breathing) parameters and/or other parameters (as discussed elsewhere herein), pressure levels, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, and/or other information. Electronic storage 130 may be a separate component within respiratory therapy device 14, or electronic storage 130 may be provided integrally with one or more other components of respiratory therapy device 14 (e.g., processor 110).

Respiratory therapy device 14 may include user interface 120 configured to provide an interface between respiratory therapy device 14 and a user (e.g., user 108, subject 106, a caregiver, a therapy decision-maker, etc.) through which the user can provide information to and receive information from respiratory therapy device 14. This enables data, results, and/or instructions and any other communicable items, collectively referred to as "information," to be communicated between the user and respiratory therapy device 14. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information is e.g. provided to subject 106 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 controls the radiation source to emit light in a manner that conveys to subject 106 information related to breathing and/or the pressurized flow of breathable gas. Note that the subject and the user of respiratory therapy device 14 may be the same person.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into respiratory therapy device 14 from removable storage (e.g., a smart card, a flash drive, a removable disk, etc.) that enables the user(s) to customize the implementation of respiratory therapy device 14. Other exemplary input devices and techniques adapted for use with respiratory therapy device 14 as user interface 120 include, but are not limited to, an RS-232 port, RF link, an IR link, modem (telephone, cable, Ethernet, internet or other). In short, any technique for communicating information with respiratory therapy device 14 is contemplated as user interface 120.

Respiratory therapy device 14 may include sensor 142 configured to generate one or more output signals conveying measurements related to respiratory parameters, including one or more of flow, pressure, humidity, velocity, acceleration, and/or other respiratory parameters. Output signals may convey measurements related to respiratory parameters. Based on these respiratory parameter, respiratory therapy device 14 (and/or any constituent components thereof) may be configured to determine one or more breathing parameters, including (tidal) volume, retrograde volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, (intentional) gas leak, and/or other breathing parameters. Sensor 142 may be in fluid communication with conduit 182 and/or subject interface appliance 184.

The illustration of sensor 142 as including a single member in FIG. 2 is not intended to be limiting. In certain embodiments sensor 142 includes a plurality of sensors operating as described above by generating output signals conveying information related to parameters associated with the gas breathed by subject 106 and/or the delivery of the gas to subject 106. For example, a breathing parameter may be related to a mechanical unit of measurement of a component of respiratory therapy device 14 such as rotor speed, motor speed, blower speed, fan speed, or a related measurement that serves as a proxy for any of the previously listed breathing parameters through a previously known/calibrated mathematical relationship. Resulting signals or information from sensor 142 may be transmitted to processor 110, user interface 120, electronic storage 130, and/or other components of respiratory therapy device 14. This transmission can be wired and/or wireless.

Processor 110 is configured to provide information processing capabilities in respiratory therapy device 14. As such, processor 110 includes one or more of a digital processor, an analog processor, a digital circuit designed to process information, an analog circuit designed to process information, a state machine, and/or other mechanisms for electronically processing information. Although processor 110 is shown in FIG. 2 as a single entity, this is for illustrative purposes only. In some implementations, processor 110 includes a plurality of processing units.

As is shown in FIG. 2, processor 110 is configured to execute one or more computer program modules. The one or more computer program modules include one or more of a control module 111, a usage module 112, a configuration module 113, a connectivity module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 2 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Control module 111 is configured to control pressure generator 140 in the provision of adjusting pressure levels for respiratory therapy device 14, to provide the pressurized flow of breathable gas at inhalation pressure levels during inhalation phases, and at exhalation pressure levels during exhalation phases.

Usage module 112 is configured to monitor, track, and/or gather therapeutic usage information for a given user associated with respiratory therapy device 14. Usage information may include one or more of a therapy starting date, user experience level, an average duration of daily usage, a usage pattern, metrics indicating quality of therapy and/or quality of sleep, level of compliance with a therapy regimen, therapeutic device characteristics (e.g. mask type or operational settings), derived usage characteristics, user-stated usage characteristics, and/or other usage information. User-stated usage characteristics may include issues or problems the user is experiencing while undergoing therapy, and/or other user-stated usage characteristics. Derived usage characteristics may include low and/or irregular usage (as detected e.g. through analysis of usage reports), decreasing usage, excessive mask leak, and/or other derived usage characteristics.

Configuration module 113 is configured to adjust mode settings and other operational parameters for respiratory therapy device 14. For example, configuration module 113 may have one set of operational parameters for a first therapy mode, and a second set of operational parameters for a second, third, or subsequent therapy mode. The first therapy mode may be an initial, default, or original therapy mode. For example, a new user (e.g. newly registered user of system 10) using respiratory therapy device 14 may start respiratory therapy by default in a particular therapy mode, such as a CPAP therapy mode.

Connectivity module 114 is configured to enable interaction between respiratory therapy device 14 and system 10. Connectivity module 114 may transmit information, such as usage information, from usage module 112 to system 10 (and/or data gathering module 22 shown in FIG. 1). Connectivity module 114 may receive commands issued and/or transmitted by system 10 (and/or device configuration module 24 shown in FIG. 1). For example, such a command may contain instructions to change a mode parameter. Connectivity module 114 may cause configuration module 113 to carry out the instructions contained in the command.

Figure 4:
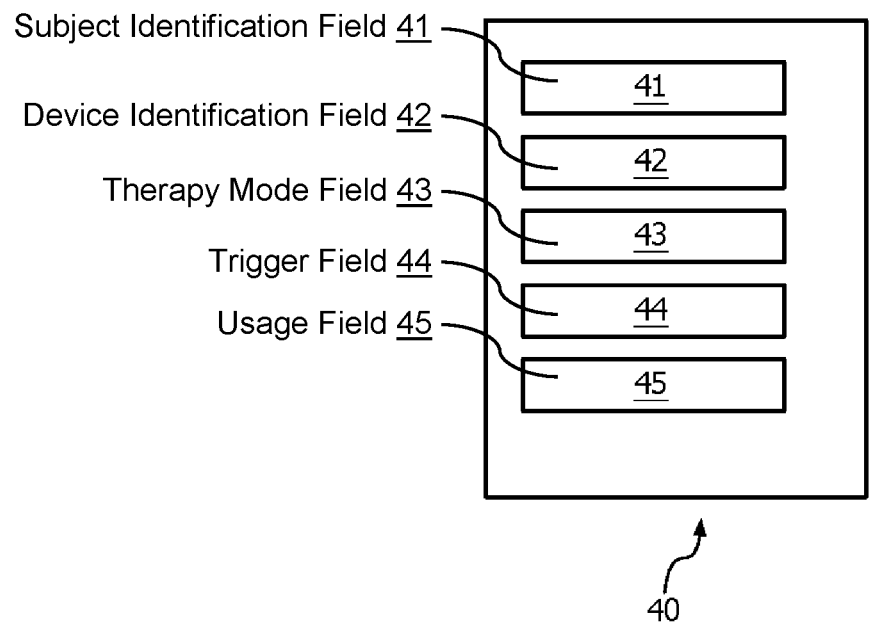
FIG. 4 illustrates an exemplary embodiment of a user interface within a respiratory therapy device capable of configuration in accordance with one or more embodiments.

FIG. 4 illustrates an exemplary embodiment of a user interface 40 within respiratory therapy device 14, capable of configuration in accordance with one or more embodiments. User interface 40 may include one or more fields configured to receive entry and/or selection of information pertaining to operational parameters and/or conditions of respiratory therapy device 14. Field 41 may be a subject identification field configured to present an identifier of the current subject associated with a given respiratory therapy device 14. Field 42 may be a device identification field configured to present an identifier of the given respiratory therapy device 14. Field 43 may be a therapy mode/activate field configured to present the current therapy mode (and/or any of the parameters/settings associated with the current therapy mode) for a given respiratory therapy device 14.

Responsive to a second therapy mode being unlocked through provider interface mode 27, field 43 may present a selectable acceptance field, e.g., labeled with an identifier and/or representation of the unlocked second therapy mode. Selection of the selectable acceptance field activates the unlocked second therapy mode for the given respiratory therapy device 14 (either indefinitely or for a trial period). Field 44 may be a message field configured to present information from a care provider, e.g. pertaining to the current respiratory therapy. Field 45 may be a usage field configured to present usage information to a user. For example, field 45 may present the average number of hours of nightly usage of a given respiratory therapy device 14 or information pertaining to the determined, measured, estimated, and/or approximated effectiveness of the current therapy mode. The same process make take place responsive to a third or subsequent therapy mode being unlocked.

Figure 5:
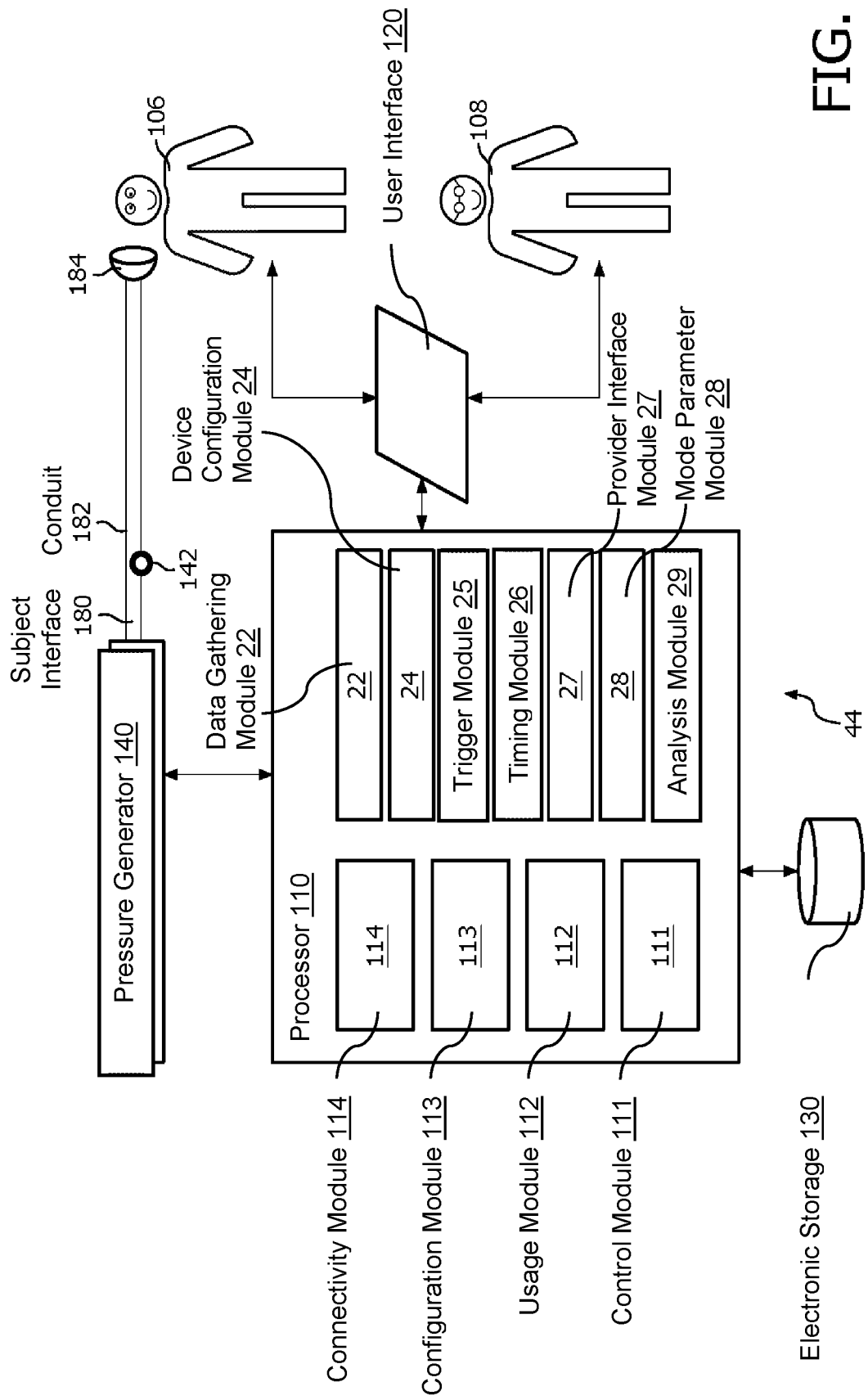
FIG. 5 schematically illustrates a respiratory therapy device capable of configuration in accordance with one or more embodiments.

FIG. 5 schematically illustrates a respiratory therapy device 44 that is capable of configuration in accordance with one or more embodiments. Respiratory therapy device 44 may comprise one or more of pressure generator 140, processor 110, sensor 142, electronic storage 130, user interface 120, subject interface 180, and/or other constituent components. Pressure generator 140, processor 110, sensor 142, electronic storage 130, user interface 120, and subject interface 180 perform the same or similar functionality as their respective counterparts in FIG. 2, described above. Respiratory therapy device 44 includes one or more of control module 111, usage module 112, configuration module 113, and/or connectivity module 114, which perform the same or similar functionality as their respective counterparts in FIG. 2, described above. Respiratory therapy device 44 may further include one or more of data gathering module 22, device configuration module 24, trigger module 25, timing module 26, provider interface module 27, mode parameter module 28, and analysis module 29, which perform the same or similar functionality as their respective counterparts in FIG. 1, described above. Respiratory therapy device 44 does not require a connection to one or more networks to perform the functionality of configuring therapy modes.

Figure 6:
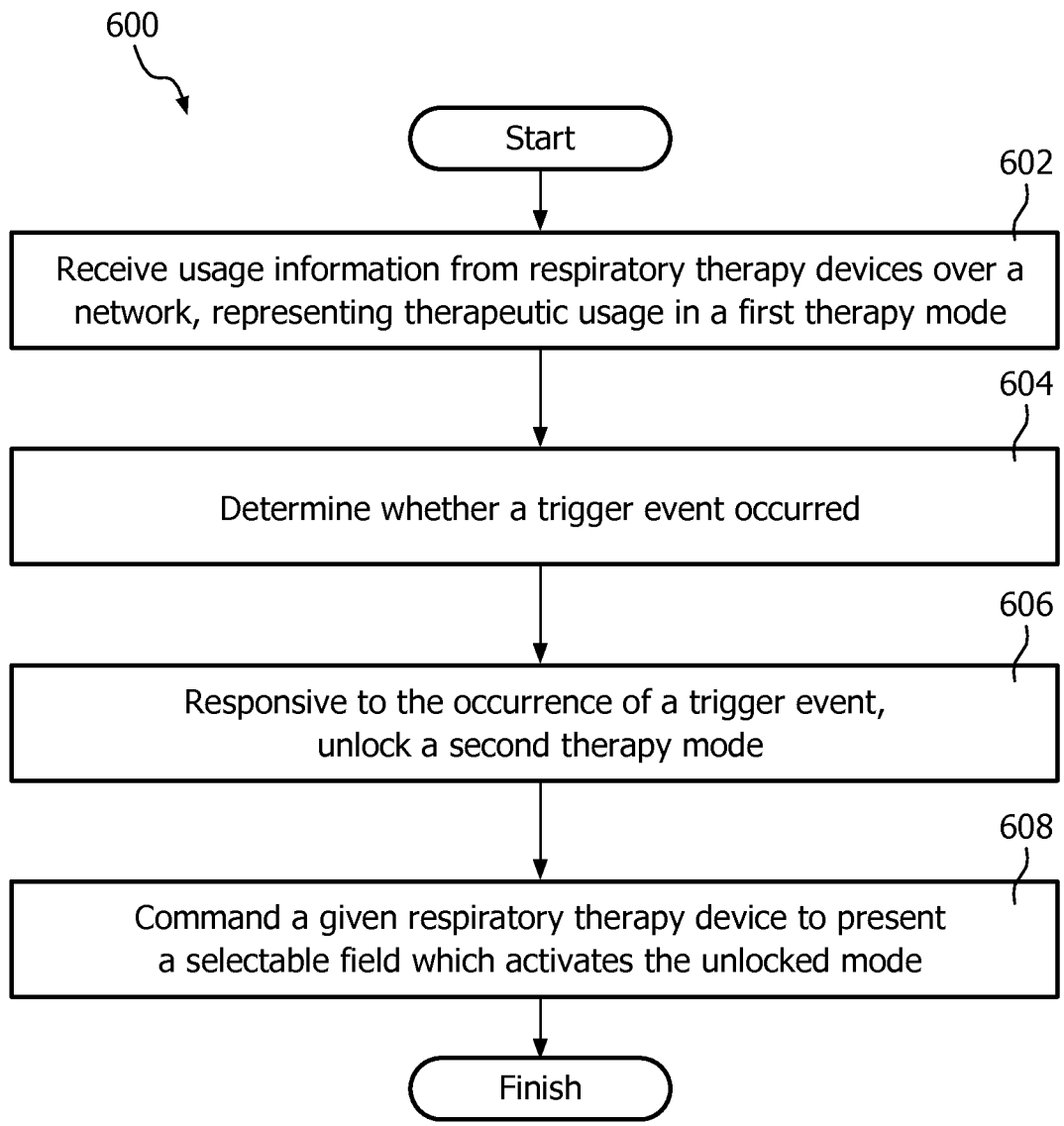
FIG. 6 illustrates a method for configuring respiratory therapy modes for users of respiratory therapy devices.

FIG. 6 illustrates a method 600 of configuring respiratory therapy modes for users of respiratory therapy devices. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, usage information is received from a respiratory therapy device, wherein the usage information represents therapeutic usage of the device in a first therapy mode. In some implementations, operation 602 may be performed by a data gathering module similar to or substantially the same as data gathering module 22 (shown in FIG. 1 and described above).

At an operation 604, the occurrence of a trigger event pertaining to a given respiratory therapy device is determined. In some implementations, operation 604 may be performed by a trigger module similar to or substantially the same as trigger module 25 (shown in FIG. 1 and described above).

At an operation 606, a second therapy mode is unlocked, responsive to the occurrence of a trigger event. In some implementations, operation 606 may be performed by a provider interface module similar to or substantially the same as provider interface module 27 (shown in FIG. 1 and described above).

At an operation 608, the respiratory therapy device is commanded to present a selectable field. Selection of the field activates the second therapy mode for the given respiratory therapy device. In some implementations, operation 608 may be performed by a device configuration module similar to or substantially the same as device configuration module 24 (shown in FIG. 1 and described above). A similar process is followed to active a third therapy mode for the given respiratory device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and that the disclosure is not limited to these embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system to configure respiratory therapy modes for users of respiratory therapy devices, the system comprising:
   one or more processors configured to execute computer program modules, the computer program modules comprising:
   (1) a data gathering module configured to receive usage information related to a respiratory therapy device in a first therapy mode, wherein the usage information received from the respiratory therapy device represents therapeutic usage of the respiratory therapy device during the first therapy mode,
   (2) an analysis module configured to determine effectiveness information related to effectiveness of therapy based on the usage information during the first therapy mode, wherein determining the effectiveness information comprises determining a respiratory disturbance index;
   (3) a provider interface module configured to receive a first unlock selection responsive to the respiratory disturbance index reaching a threshold, the first unlock selection being received while the respiratory therapy device is operating in the first therapy mode, the first unlock selection indicating that a second therapy mode for the respiratory therapy device should be unlocked, wherein the second therapy mode is different than the first therapy mode, and the second therapy mode is not available for use on the respiratory therapy device prior to reception of the first unlock selection; and (4) a device configuration module configured such that, responsive to reception of the first unlock selection by the provider interface module, the device configuration module activates the second therapy mode for the respiratory therapy device, wherein the device configuration module is further configured to deactivate the second therapy mode after a predetermined trial period has expired.

2. The system of claim 1, wherein the device configuration module is further configured such that, responsive to reception of the first unlock selection, the device configuration module causes the respiratory therapy device to activate a selectable acceptance field, wherein user selection of the selectable acceptance field indicates acceptance of the second therapy mode, and wherein activation of the second therapy mode for the respiratory therapy device is further responsive to user selection of the selectable acceptance field.

3. The system of claim 1, further comprising a trigger module configured to determine whether a trigger event occurred pertaining to the respiratory therapy device based on the determination of the effectiveness information by the analysis module.

4. The system of claim 3, wherein the trigger event is based on the usage information.

5. The system of claim 1, wherein the unlocked second therapy mode includes one or both of a multi-pressure-level mode and/or an auto-titrating mode.

6. The system of claim 1, wherein determining the respiratory disturbance index comprises determining the index based on a number of apneas, a number of hypopneas, and a number of respiratory effort related arousals in a given time period during the first therapy mode.

7. The system of claim 1, wherein deactivation of the second therapy mode comprises activation of a third therapy mode, and wherein the second therapy mode is not available for use on the respiratory therapy device after deactivation of the second therapy mode.

8. A method to configure respiratory therapy modes for users of respiratory therapy devices, the method comprising:
receiving usage information related to a respiratory therapy device in a first therapy mode, wherein the received usage information represents therapeutic usage of the respiratory therapy device during the first therapy mode;
determining effectiveness information related to effectiveness of therapy based on the usage information during the first therapy mode, wherein determining the effectiveness information comprises determining a respiratory disturbance index;
receiving a first unlock selection responsive to the respiratory disturbance index reaching a threshold, the first unlock selection being received while the respiratory therapy device is operating in the first therapy mode, the first unlock selection indicating that a second therapy mode for the respiratory therapy device should be unlocked, wherein
the second therapy mode is different than the first therapy mode, and
the second therapy mode is not available for use on the respiratory therapy device prior to reception of the first unlock selection;

responsive to reception of the first unlock selection, activating the second therapy mode for the respiratory therapy device; and
responsive to expiration of a predetermined trial period, deactivating the second therapy mode for the respiratory therapy device.

9. The method of claim 8, wherein activating the second therapy mode includes:
causing the respiratory therapy device to activate a selectable acceptance field, wherein user selection of the selectable acceptance field indicates acceptance of the second therapy mode, and
responsive to user selection of the selectable acceptance field, activating the second therapy mode.

10. The method of claim 8, further comprising determining whether a trigger event pertaining to the respiratory therapy device occurred based on the determination of the effectiveness information.

11. The method of claim 10, wherein the trigger event is based on the usage information from the respiratory therapy device.

12. The method of claim 8, wherein the second therapy mode includes one or both of a multi-pressure-level mode and/or an auto-titrating mode.

13. The method of claim 8, wherein determining the respiratory disturbance index comprises determining the index based on a number of apneas, a number of hypopneas, and a number of respiratory effort related arousals in a given time period during the first therapy mode.

14. A system for configuring respiratory therapy modes for users of respiratory therapy devices, the system comprising:
means for receiving usage information related to a respiratory therapy device in a first therapy mode, and wherein the received usage information represents therapeutic usage of the respiratory therapy device during the first therapy mode;
means for determining effectiveness information related to effectiveness of therapy based on the usage information during the first therapy mode, wherein determining the effectiveness information comprises determining a respiratory disturbance index;
means for receiving a first unlock selection responsive to the respiratory disturbance index reaching a threshold, the first unlock selection being received while the respiratory therapy device is operating in a first therapy mode, the first unlock selection indicating a second therapy mode for the respiratory therapy device should be unlocked, wherein
the second therapy mode is different than the first therapy mode, and
the second therapy mode is not available for use on the respiratory therapy device prior to reception of the first unlock selection; and
means for activating the second therapy mode responsive to reception of the first unlock selection and for deactivating the second therapy mode responsive to expiration of a predetermined trial period.

15. The system of claim 14, wherein the means for activating the second therapy mode includes:
means for causing the respiratory therapy device to activate a selectable acceptance field, wherein user selection of the selectable acceptance field indicates acceptance of the second therapy mode, and
means for activating the second therapy mode, responsive to user selection of the selectable acceptance field.

16. The system of claim 14, further comprising means for determining whether a trigger event pertaining to the respiratory therapy device occurred based on the determination of the effectiveness information by the means for determining effectiveness information.

17. The system of claim 16, wherein the trigger event is based on the usage information from the respiratory therapy device.

18. The system of claim 14, wherein the second therapy mode includes one or both of a multi-pressure-level mode and/or an auto-titrating mode.

19. The system of claim 14, wherein determining the respiratory disturbance index comprises determining the index based on a number of apneas, a number of hypopneas, and a number of respiratory effort related arousals in a given time period during the first therapy mod.

* * * * *